United States Patent [19]

Pohl et al.

[11] Patent Number: 5,487,357
[45] Date of Patent: Jan. 30, 1996

[54] BORON-CONTAINING ORGANIC GROUP-V COMPOUNDS USEFUL FOR GAS PHASE DEPOSITION OF THE GROUP-V ELEMENT ON SUBSTRATES

[75] Inventors: Ludwig Pohl, Darmstadt; Herbert Schumann; Christian Marschall, both of Berlin, all of Germany

[73] Assignee: Merck Patent Gesellschaft Mit Beschrankter Haftung, Darmstadt, Germany

[21] Appl. No.: 190,028

[22] PCT Filed: May 19, 1993

[86] PCT No.: PCT/EP93/01241

§ 371 Date: Jan. 28, 1994

§ 102(e) Date: Jan. 28, 1994

[87] PCT Pub. No.: WO93/24675

PCT Pub. Date: Dec. 9, 1993

[30] Foreign Application Priority Data

May 29, 1992 [DE] Germany ............ 42 17 735.9

[51] Int. Cl.⁶ .................. C23C 16/18; C23C 16/38
[52] U.S. Cl. .............. 117/104; 427/248.1; 427/250; 427/252
[58] Field of Search .................. 427/248.1, 250, 427/252; 117/104

[56] References Cited

U.S. PATENT DOCUMENTS

| | | | |
|---|---|---|---|
| 4,946,713 | 8/1990 | Sneddon et al. | 427/226 |
| 4,975,299 | 12/1990 | Mir et al. | 427/226 |
| 5,082,693 | 1/1992 | Paine, Jr. et al. | 427/226 |
| 5,126,168 | 6/1992 | Sneddon et al. | 427/255 |
| 5,139,999 | 8/1992 | Gordon et al. | 427/255.3 |
| 5,209,952 | 5/1993 | Erdmann et al. | 427/255.6 |
| 5,234,716 | 8/1993 | Hostalek et al. | 427/255.6 |
| 5,277,932 | 1/1994 | Spencer | 427/255.2 |

FOREIGN PATENT DOCUMENTS 0450125  10/1991  European Pat. Off. .

*Primary Examiner*—Shrive Beck
*Attorney, Agent, or Firm*—Millen, White, Zelano, & Branigan

[57] ABSTRACT

The invention relates to the use of boron-containing organic group-V compounds for the deposition of the elements of the Vth main group on substrates by gas-phase deposition.

9 Claims, No Drawings

BORON-CONTAINING ORGANIC GROUP-V COMPOUNDS USEFUL FOR GAS PHASE DEPOSITION OF THE GROUP-V ELEMENT ON SUBSTRATES

The invention relates to the use of boron-containing organic group-V compounds for the preparation of thin films or epitaxial layers by the deposition of the elements of the Vth main group on substrates by gas-phase deposition.

The deposition of such layers consisting of either pure elements of the Vth group or usually of combinations with other elements such as, e.g., gallium arsenide, indium phosphide or gallium phosphide can be used for the fabrication of electrical, electronic, optical or optoelectronic switching elements, compound semiconductors and lasers. The deposition of these layers is carried out from the gas phase.

The properties of these films depend on the deposition conditions and the chemical composition of the deposited film.

Possible deposition methods from the gas phase include all the known methods such as the metal-organic chemical vapor deposition (MOCVD) method, the plasma-enhanced metal-organic chemical vapor deposition (PE-MOCVD) method, the photo-metal-organic vapor phase (photo-MOVP) method, in which the substances are decomposed by UV irradiation, the laser chemical vapor deposition (laser CVD) method or the metal-organic magnetron scattering (MOMS) method. The advantages compared to other methods are controllable layer growth, accurately controlled doping and, owing to the atmospheric-pressure or low-pressure conditions, simple handling and uncomplicated production. This method further permits simple mass production.

BACKGROUND OF THE INVENTION

The MOCVD method employs organometallic compounds which decompose at a temperature below 1100° C. with the deposition of the metal. Typical equipment which at present is used for MOCVD consists of a "bubbler" with a supply for the organometallic components, a reaction chamber which contains the substrate to be coated and a source for a carrier gas which should be inert with respect to the organometallic component. The "bubbler" is maintained at a constant, relatively low temperature which is preferably above the melting point of the organometallic compound, but far below the decomposition temperature. The reaction or decomposition chamber preferably has a much higher temperature, which is below 1100° C., at which the organometallic compound decomposes completely and the metal is deposited. By means of the carrier gas, the organometallic compound is converted to the vapor state and, together with the carrier gas, transferred into the decomposition chamber. The mass flow of the vapor is easily controlled, and this also permits controlled growth of the thin layer.

The other methods of gas phase deposition essentially differ therefrom only by the manner in which the energy required for the decomposition is supplied.

Hitherto the standard MOCVD processes for generating layers containing elements of group V have mainly employed, for example, $AsH_3$ or $PH_3$, which do however have major drawbacks such as toxicity and spontaneous inflammability. Their preparation, transport, storage, and the use of these compounds therefore requires elaborate safety precautions.

SUMMARY OF THE INVENTION

The object of the present invention is therefore to find suitable alternative, preferably liquid, group-V organyls which are no longer pyrophoric but which can be decomposed from the gas phase, which are therefore suitable for the various methods of gas-phase deposition and, in particular, subject to drastically reduced general potential hazards.

We have found that with the aid of borane derivatives both inter- and intramolecular adduct formation with elements of the Vth main group is possible which results in coordinatively saturated, low-melting and chemically stable organometalloid compounds, which have a vapor pressure suitable for gas-phase deposition processes, are no longer spontaneously flammable and thus eminently meet the abovementioned requirements.

The invention therefore relates to the use of boron-containing organic group-V compounds for the deposition of the elements of the Vth main group on substrates by gas-phase deposition and to a process for preparing thin films or layers on substrates by element deposition from the gas phase, in which boron-containing organic group-V compounds are employed for the deposition of elements of the Vth main group.

The invention further relates to the procedure of feeding in, during the deposition process, other organometallic compounds which are gaseous under the reaction conditions used.

The boron-containing organic group-V compounds preferably correspond to the formulae I, II, III or IV wherein,

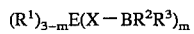

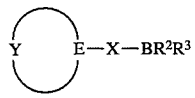

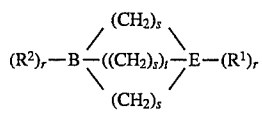

E is nitrogen, phosphorus, arsenic or antimony, m is 1, 2 or 3,

X is $—(CHR^4)_n—$

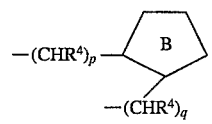

A is a phenyl, cyclohexyl, cyclohexenyl or cyclohexadienyl ring,

B is a cyclopentyl, cyclopentenyl or cyclopentadienyl ring, n is 1, 2, 3, 4, 5 or 6, p and q are each, independently of one another, 0, 1, 2, 3 or 4, Y is an alkylene or alkylidene group having 3–7 C atoms, in which one or more H atoms may be replaced by $R^5$, it being possible for one or more non-adjacent double bonds to be present in the alkylidene group, s in each case is 1, 2, 3 or 4, r and t are each 0 or 1, whilst r+t is 1, $R^1$, $R^2$, $R^3$, $R^5$ and $R^6$ are each, independently of one another, H, an alkyl group having up to 8 C atoms, which group may be partially or completely fluorinated, a cycloalkyl or cycloalkenyl group having 3–8 C atoms or an aryl group and R⁴ in each case is H or an alkyl group having 1–4 C atoms which may also be partially or completely fluorinated.

The coordinative saturation of the group-V elements can be achieved intramolecularly, as in the compounds of the formulae I, II and IV, or intermolecularly as in the adducts of the formula III. In all cases, these compounds represent low-melting and chemically stable compounds which are no longer spontaneously inflammable and have a vapor pressure which is suitable for gas-phase deposition.

As a result, they are compounds which are easily handled and which can be employed particularly advantageously for the MOCVD technique and make the fabrication process of compound semiconductor components considerably safer.

The compounds according to the invention contain as the group-V element preferably nitrogen, phosphorus, arsenic or antimony.

In the formulae I, II, III and IV, E is particularly preferably P, As or Sb.

The radicals $R^1$, $R^2$, $R^3$, $R^5$ and $R^6$ in the formulae I, II, III and IV are each preferably H or a straight-chain or branched alkyl group having 1–8 C atoms, preferably 1–5 C atoms. The alkyl groups are preferably straight-chain and accordingly are preferably methyl, ethyl, propyl, butyl, pentyl, also hexyl, heptyl, octyl, iso-propyl, sec-butyl, tert-butyl, 2-methylpentyl, 3-methylpentyl or 2-octyl. The alkyl radicals may be partially or completely fluorinated and, for example, are monofluoromethyl, trifluoromethyl, difluoroethyl, trifluoroethyl, pentafluoroethyl, heptafluoropropyl, nonafluorobutyl, undecafluoropentyl or trifluoropropyl. Preferably, only one or two radicals are H.

If $R^1$, $R^2$, $R^3$, $R^5$ and/or $R^6$ are a cycloalkyl or cycloalkenyl group having 3–8 C atoms, they are preferably cyclopropyl, cyclobutyl, cyclopentyl, cyclopentenyl, cyclohexyl, cyclohexenyl, cyclohexadienyl, cycloheptyl, cycloheptenyl, cycloheptadienyl, cyclooctyl, cyclooctenyl, cyclooctadienyl, cyclooctatrienyl or cyclooctatetraenyl.

Further, compounds of the formulae I to IV are preferred in which $R^1$, $R^2$, $R^3$, $R^5$ and/or $R^6$ are an aryl group. In this context, aryl preferably means a phenyl group. This phenyl group can also be present in the substituted form. As these substituents do not have a significant influence on the intended application, all substituents are permitted which do not have an adverse effect on the decomposition reaction.

In formula I, m is 1, 2 or 3, preferably 1 or 2.

X in formula I is preferably —(CHR⁴)$_n$—, where n= 1, 2, 3, 4, 5 or 6, and preferably n=2, 3 or 4.

If n=1, stabilization is usually accomplished intermolecularly.

$R^4$ is either an H atom or preferably a straight-chain alkyl group which may be partially or completely fluorinated, having 1–4 C atoms and is therefore preferably methyl, ethyl, propyl, butyl, trifluoromethyl, tetrafluoroethyl, pentafluoroethyl or heptafluoropropyl. If $R^4$ is an alkyl or a partially or completely fluorinated alkyl group, preferably only one $R^4$ in —(CHR⁴)$_n$— is an alkyl group, the others in that case being H.

Further, compounds of the formula I are preferred in which X is

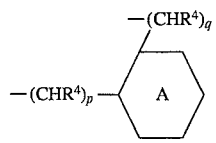

or

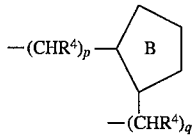

in which p and q are each, independently of one another, 0, 1, 2, 3 or 4, preferably 0, 1 or 2. p+q is preferably 0, 1, 2, 3 or 4, particularly preferably 1 or 2.

A is preferably a phenyl or cyclohexyl ring, alternatively a cyclohexenyl or cyclohexadienyl ring, any arrangement of the double bonds in the cyclohexane ring being permitted.

B is preferably a cyclopentyl or cyclopentadienyl ring, alternatively a cyclopentenyl ring, in this case any arrangement of the double bonds in the ring is being permitted.

In the compounds of the formula I there are present, depending on the meaning of m, a plurality of groups $R^1$ and (X—BR²R³), respectively. These groups may then in each case have different or identical meanings. Preferably, the $R^1$ groups and the (X—BR²R³) radicals, respectively, have identical meanings.

Exemplary representatives of the compounds of formula I are those of the formulae I1 to I60:

| | |
|---|---|
| (R¹)₂N—(CHR⁴)$_n$—BR²R³ | I1 |
| (R¹)₂P—(CHR⁴)$_n$—BR²R³ | I2 |
| (R¹)₂As—(CHR⁴)$_n$—BR²R³ | I3 |
| (R¹)₂Sb—(CHR⁴)$_n$—BR²R³ | I4 |
| (R¹)₂N—(CH₂)$_n$—BR²R³ | I5 |
| (R¹)₂P—(CH₂)$_n$—BR²R³ | I6 |
| (R¹)₂As—(CH₂)$_n$—BR²R³ | I7 |
| (R¹)₂Sb—(CH₂)$_n$—BR²R³ | I8 |

I9

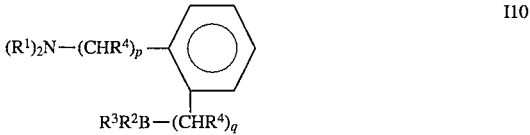

I10

I11

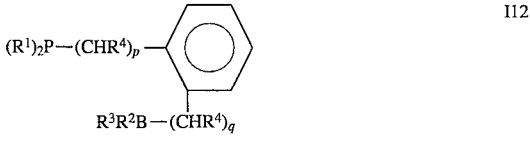

I12

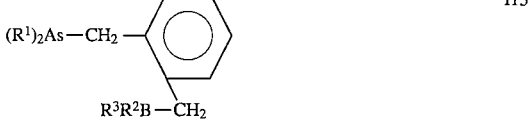

I13

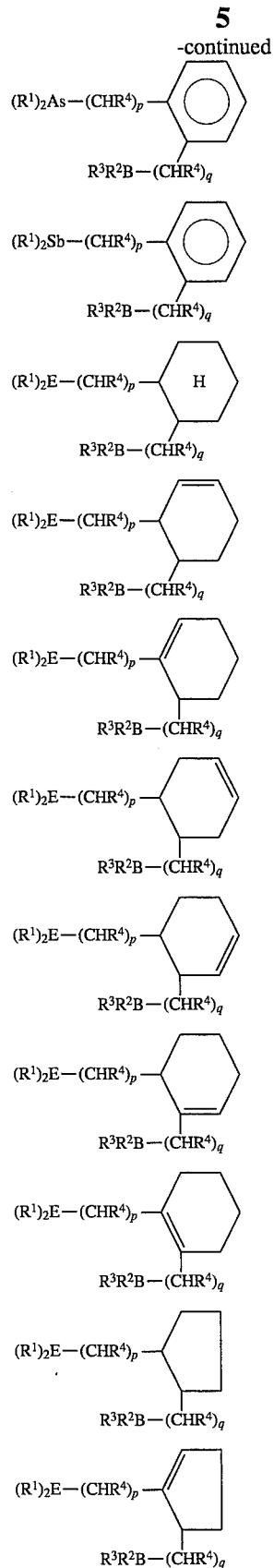
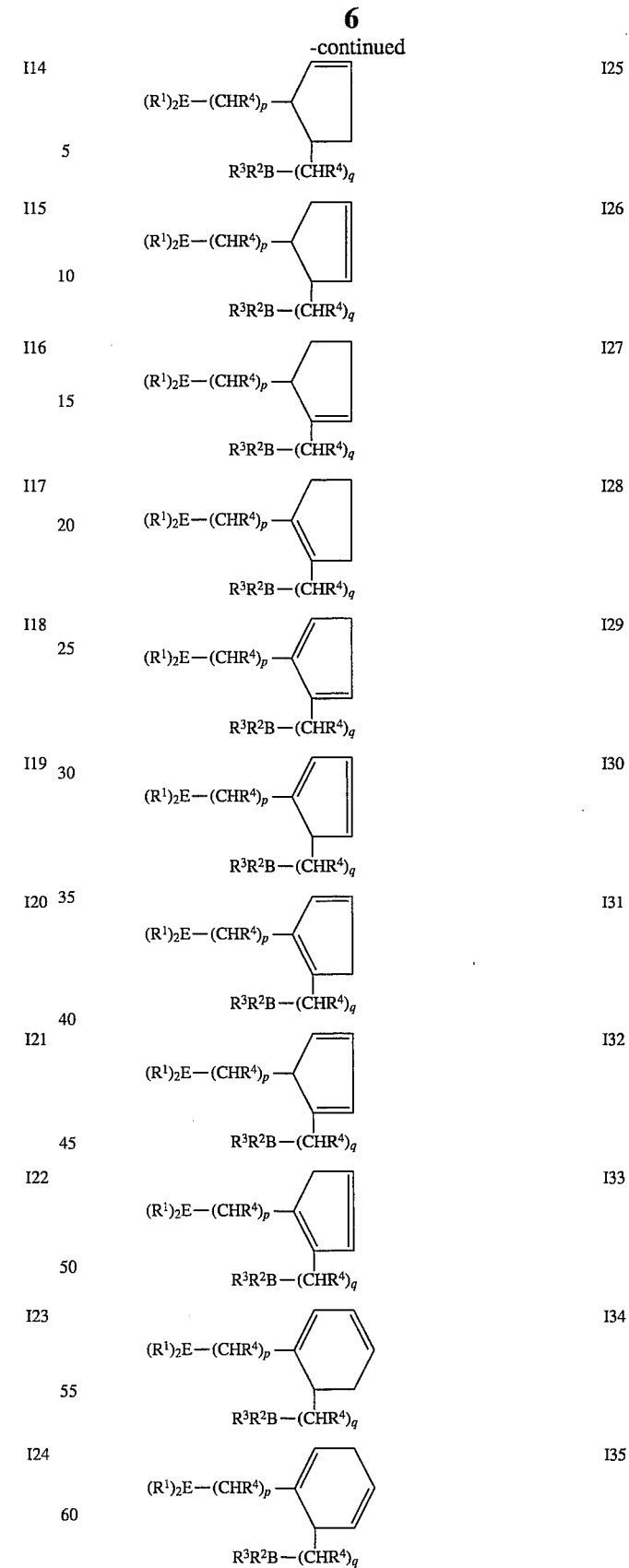

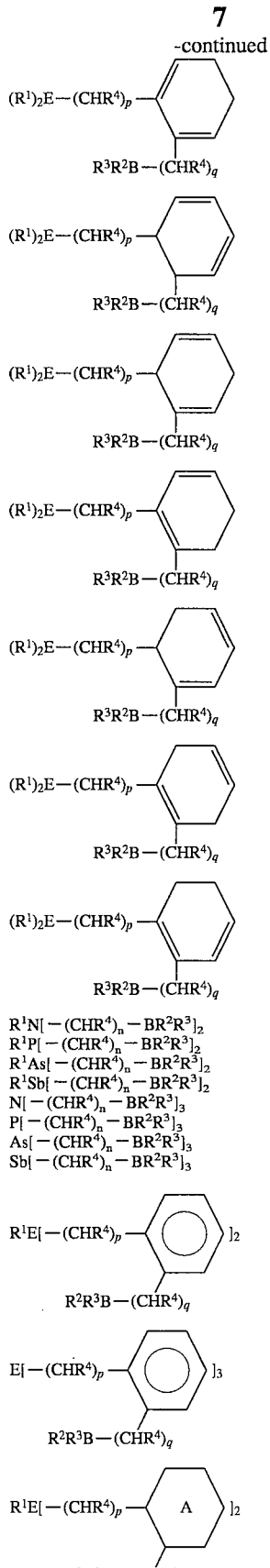

```
R¹N[—(CHR⁴)ₙ—BR²R³]₂
R¹P[—(CHR⁴)ₙ—BR²R³]₂
R¹As[—(CHR⁴)ₙ—BR²R³]₂
R¹Sb[—(CHR⁴)ₙ—BR²R³]₂
N[—(CHR⁴)ₙ—BR²R³]₃
P[—(CHR⁴)ₙ—BR²R³]₃
As[—(CHR⁴)ₙ—BR²R³]₃
Sb[—(CHR⁴)ₙ—BR²R³]₃
```

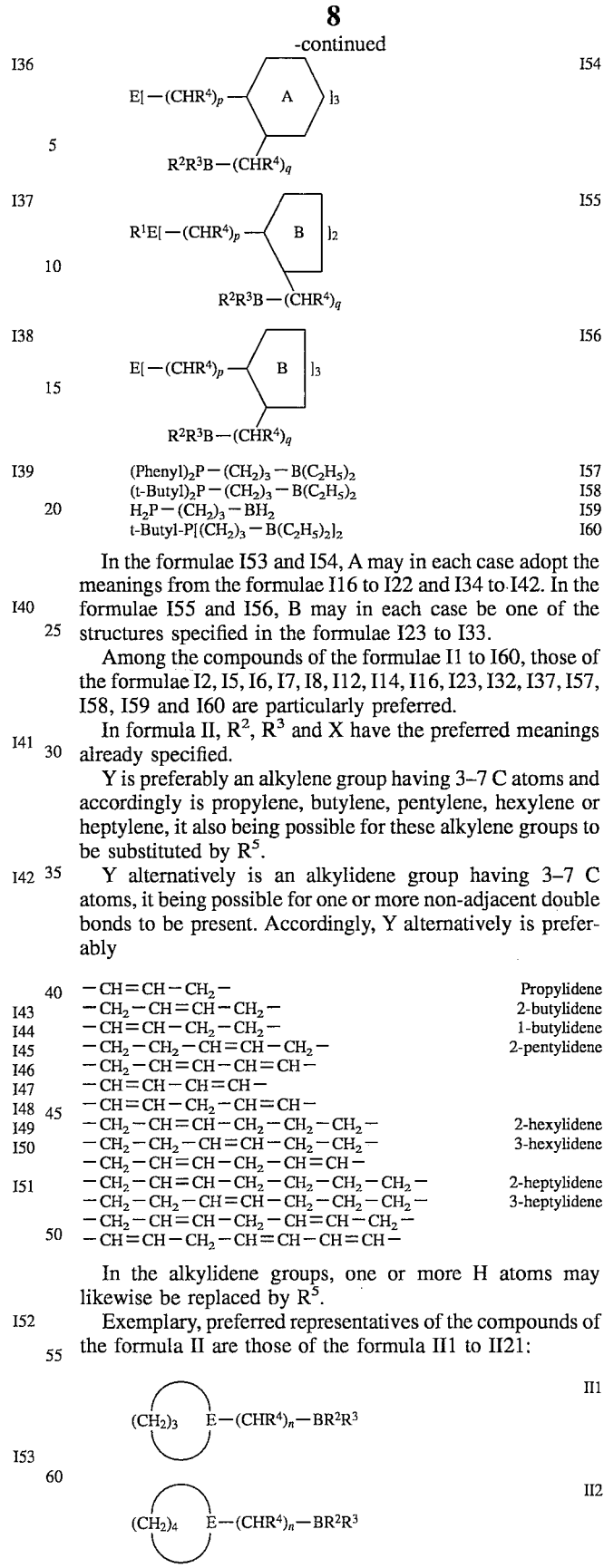

| | |
|---|---|
| (Phenyl)₂P—(CH₂)₃—B(C₂H₅)₂ | I57 |
| (t-Butyl)₂P—(CH₂)₃—B(C₂H₅)₂ | I58 |
| H₂P—(CH₂)₃—BH₂ | I59 |
| t-Butyl-P[(CH₂)₃—B(C₂H₅)₂]₂ | I60 |

In the formulae I53 and I54, A may in each case adopt the meanings from the formulae I16 to I22 and I34 to I42. In the formulae I55 and I56, B may in each case be one of the structures specified in the formulae I23 to I33.

Among the compounds of the formulae I1 to I60, those of the formulae I2, I5, I6, I7, I8, I12, I14, I16, I23, I32, I37, I57, I58, I59 and I60 are particularly preferred.

In formula II, $R^2$, $R^3$ and X have the preferred meanings already specified.

Y is preferably an alkylene group having 3–7 C atoms and accordingly is propylene, butylene, pentylene, hexylene or heptylene, it also being possible for these alkylene groups to be substituted by $R^5$.

Y alternatively is an alkylidene group having 3–7 C atoms, it being possible for one or more non-adjacent double bonds to be present. Accordingly, Y alternatively is preferably

| | |
|---|---|
| —CH=CH—CH₂— | Propylidene |
| —CH₂—CH=CH—CH₂— | 2-butylidene |
| —CH=CH—CH₂—CH₂— | 1-butylidene |
| —CH₂—CH₂—CH=CH—CH₂— | 2-pentylidene |
| —CH₂—CH=CH—CH=CH— | |
| —CH=CH—CH=CH— | |
| —CH=CH—CH₂—CH=CH— | |
| —CH₂—CH=CH—CH₂—CH₂—CH₂— | 2-hexylidene |
| —CH₂—CH₂—CH=CH—CH₂—CH₂— | 3-hexylidene |
| —CH₂—CH=CH—CH₂—CH=CH— | |
| —CH₂—CH=CH—CH₂—CH₂—CH₂—CH₂— | 2-heptylidene |
| —CH₂—CH₂—CH=CH—CH₂—CH₂—CH₂— | 3-heptylidene |
| —CH₂—CH=CH—CH₂—CH=CH—CH₂— | |
| —CH=CH—CH₂—CH=CH—CH=CH— | |

In the alkylidene groups, one or more H atoms may likewise be replaced by $R^5$.

Exemplary, preferred representatives of the compounds of the formula II are those of the formula II1 to II21:

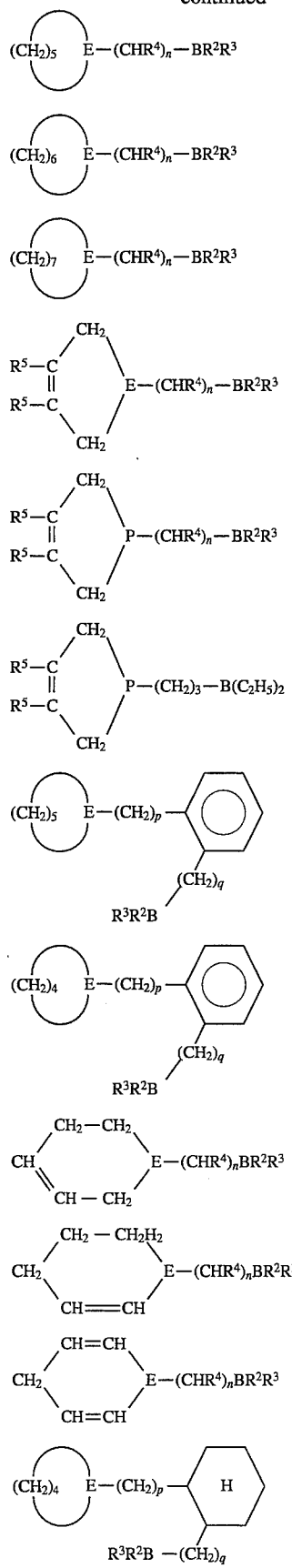

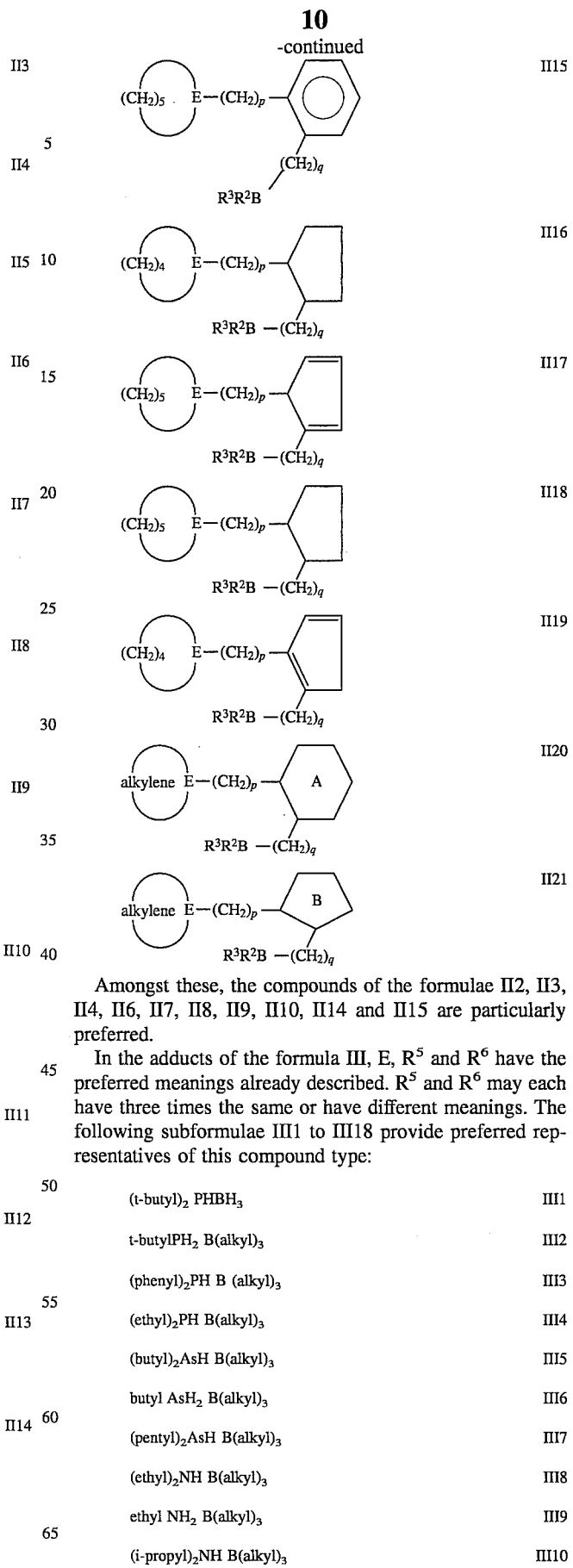

Amongst these, the compounds of the formulae II2, II3, II4, II6, II7, II8, II9, II10, II14 and II15 are particularly preferred.

In the adducts of the formula III, E, $R^5$ and $R^6$ have the preferred meanings already described. $R^5$ and $R^6$ may each have three times the same or have different meanings. The following subformulae III1 to III18 provide preferred representatives of this compound type:

| | |
|---|---|
| (t-butyl)$_2$ PHBH$_3$ | III1 |
| t-butylPH$_2$ B(alkyl)$_3$ | III2 |
| (phenyl)$_2$PH B (alkyl)$_3$ | III3 |
| (ethyl)$_2$PH B(alkyl)$_3$ | III4 |
| (butyl)$_2$AsH B(alkyl)$_3$ | III5 |
| butyl AsH$_2$ B(alkyl)$_3$ | III6 |
| (pentyl)$_2$AsH B(alkyl)$_3$ | III7 |
| (ethyl)$_2$NH B(alkyl)$_3$ | III8 |
| ethyl NH$_2$ B(alkyl)$_3$ | III9 |
| (i-propyl)$_2$NH B(alkyl)$_3$ | III10 |

| | |
|---|---|
| (cyclohexyl)$_2$EH B(alkyl)$_3$ | III11 |
| (phenyl)$_2$EH B(alkyl)$_3$ | III12 |
| (phenyl)$_3$E B(alkyl)$_3$ | III13 |
| methyl EH$_2$ B(alkyl)$_3$ | III14 |
| (ethyl)$_3$E B(alkyl)$_3$ | III15 |
| (phenyl)$_2$SbH B(alkyl)$_3$ | III16 |
| (alkyl)$_3$E B(phenyl)$_3$ | III17 |
| (ethyl) (propyl)EH B(alkyl)$_3$ | III18 |

The compounds of the formula IV have a cyclic or bicyclic structure and are stabilized intramolecularly.

In formula IV, E, $R^1$ and $R^2$ each represent the preferred groups already described.

s in the $(CH_2)_s$ groups may be, independently of one another, 1, 2, 3 or 4. Preferably, s is 2 or 3, and preferably s has identical meanings in the $(CH_2)$ groups.

r and t may each be 0 or 1, with r+t=1. Preferably, r=1 and t=0.

The following group of compounds show preferred representatives of this class of substances:

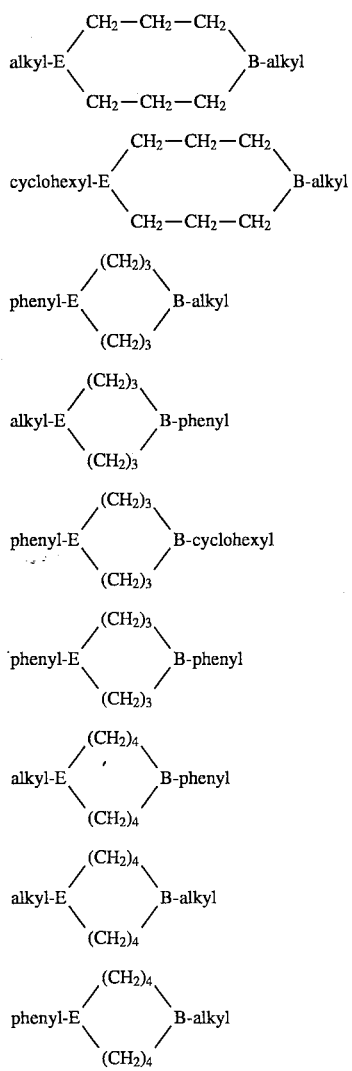
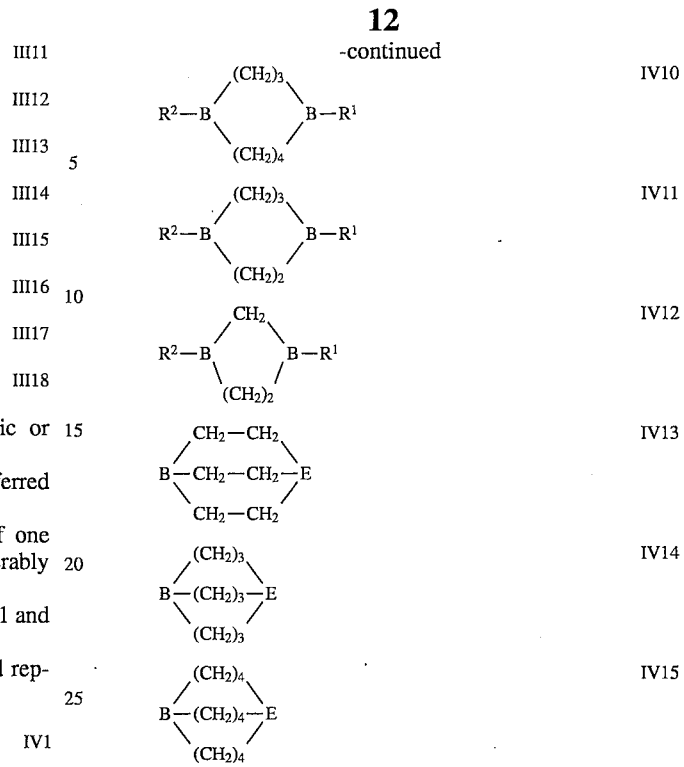

The compounds of the formulae I, II, III and IV are eminently suitable for MOCVD epitaxy, as they are simple to handle and decompose at elevated temperatures, liberating the corresponding element. They are also suitable for the other gas phase deposition methods.

The boron-containing organic group-V compounds are prepared by methods known per se as described in the literature (e.g. Houben-Weyl, Methoden der organischen Chemie, [Methods of organic chemistry], Georg Thieme Verlag, Stuttgart) specifically under reaction conditions which are known and suitable for the reactions mentioned. It is also possible, in this context, to make use of variations known per se which are not mentioned here in any detail.

For example, adducts of the formula III can be prepared by direct reaction of the corresponding boron compounds $B(R^6)_3$ with the compounds containing the Vth group element, $E(R^5)_3$.

It is further possible to prepare the compounds of the formulae I, II and IV, for example, by employing appropriate boron(alkyl)chlorides with an appropriate Grignard compound or an alkali metal organyl of the appropriate group-V Lewis base in an inert solvent.

The reactions are preferably carried out in inert solvents. All those solvents can be used for this purpose which do not adversely affect the reaction and do not interfere with the reaction mechanism, such as, for example, diethylether or tetrahydrofuran. The reaction temperatures essentially correspond to those which are known from the literature for the preparation of similar compounds.

In the process according to the invention for preparing thin films or epitaxial layers on any substrates, the gas-phase deposition processes known per se employ, for the purpose of depositing elements of the Vth main group, boron-containing organic group-V compounds, preferably those of the formulae I, II, III or IV. The reaction conditions can be chosen in analogy to those known from the literature and familiar to those skilled in the art.

For the purpose of fabricating compound semiconductors, electrical, electronic, optical and optoelectronic components it is possible to admix in the decomposition chamber, in the process according to the invention during the deposition process, one or more compounds which are gaseous under the reaction conditions used, of other elements of the Periodic Table of the Elements, preferably organometallic compounds of aluminum, gallium or indium. A further variation of the process according to the invention comprises the additional admixture of dopants during the deposition process. The dopants employed in the process are volatile organometallic compounds of iron, magnesium, zinc or chromium. Compounds considered to be conventional in this context include $Zn(CH_3)_2$, $Mg(CH_3)_2$ or $Fe(C_5H_5)_2$.

The following examples are intended to explain the invention in more detail. Temperatures are given in degrees Celsius. M.p. means melting point and b.p. boiling point.

EXAMPLE 1

A suspension of 5.98 g (73 mmol) of $(CH_3)_2PCH_2Li$ (prepared by reacting $P(CH_3)_3$ with tert-$C_4H_9Li$) in 100 ml of tetrahydrofuran is admixed, slowly and dropwise at −10° C., with 7.61 g (73 mmol) of $ClB(C_2H_9)_2$ (which can be prepared by reacting $Al(C_2H_5)_3$ with $BCl_3$) in 200 ml of tetrahydrofuran. After the addition is complete, the mixture is stirred for another two hours at room temperature, before stripping off the solvent on a vacuum pump. The residue is then taken up in benzene and freed of the precipitate by washing a number of times with degassed water. The combined organic phases are dried with sodium sulfate, freed of the drying agent and again concentrated on a vacuum pump. The residue is finally taken up in pentane. A white precipitate of dimethylphosphinodiethylboramethane is formed, m.p. 120.1° C.

EXAMPLE 2

A flask is charged with 6.09 g (37.75 mmol) of diphenylphosphane (prepared by reaction of $LiAlH_4$ [sic] with $(C_6H_5)_2PCl$) and the contents are heated to approximately 110° C. 3.61 g (32.8 mmol) of diethylallylborane (obtained by reacting $(C_2H_5)_2BCl$ with $C_3H_5MgBr$) are now slowly added dropwise. The solution is then boiled for another 5 hours at 200° C. under reflux. After the reaction mixture has cooled down, the oily residue is subjected to fractional distillation. The product $(C_6H_5)_2PCH_2CH_2CH_2B(C_2H_5)_2$ distils into the receiver in the form of a colorless liquid at 145° C. and 0.06 mbar and is stored under argon at −10° C.

We claim:

1. A method which comprises subjecting a boron-containing, Group VA element-containing organic compound to gas-phase deposition conditions in the presence of a substrate to deposit a Group VA element on the substrate wherein the boron-containing, Group VA element-containing organic compound is a compound of one of the following formulae:

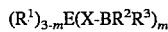

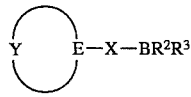

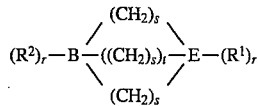

wherein

E is nitrogen, phosphorus, arsenic or antimony, m is 1, 2 or 3,

X is $—(CHR^4)_n—$

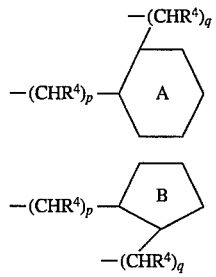

A is a phenyl, cyclohexyl, cyclohexenyl or cyclohexadienyl ring,

B is a cyclopentyl, cyclopentenyl or cyclopentadienyl ring, n is 1, 2, 3, 4, 5 or 6, p and q are each, independently of one another, 0, 1, 2, 3, or 4, Y is an alkylene or alkylidene group having 3–7 C atoms, in which one or more H atoms may be replaced by $R^5$, and, optionally, one or more non-adjacent double bonds are present in the alkylidene group, s in each case is 1, 2, 3 or 4, r and t are each 0 or 1, while r+t is 1, $R^1$, $R^2$ and $R^3$ are each, independently of one another, H, an alkyl group having 1 to 8 C atoms, which group may be partially or completely fluorinated, a cycloalkyl or cycloalkenyl group having 3–8 C atoms or an aryl group and $R^4$ in each case is H or an alkyl group having 1–4 C atoms which may also be partially or completely fluorinated.

2. The method of claim 1, wherein the Group VA element is deposited on the substrate as at least one epitaxial layer.

3. The method of claim 1, wherein the substrate is an electrical, electronic, optical or electrooptical component.

4. The method of claim 1, wherein another organometallic compound which is gaseous under the deposition conditions is present with the boron-containing organic Group VA compound.

5. The method of claim 1, wherein the Group VA element is nitrogen, phosphorus, arsenic or antimony.

6. The method of claim 1, wherein the element of Group VA is nitrogen, phosphorus or arsenic.

7. In a process for preparing a substrate with a layer thereon by element deposition from the gas phase, the improvement wherein a boron-containing Group VA element-containing compound of one of the following formula I, II, III or IV is employed for the deposition of a Group VA element-containing compound is a compound of one of the following formulae I, II, III or IV:

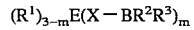     I

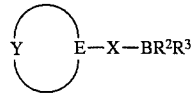     II

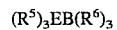     III

-continued

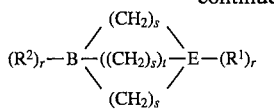   IV wherein

E is nitrogen, phosphorus, arsenic or antimony, m is 1, 2 or 3,

X is —(CHR⁴)$_n$—

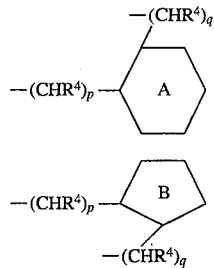

A is a phenyl, cyclohexyl, cyclohexenyl or cyclohexadienyl ring,

B is a cyclopentyl, cyclopentenyl or cyclopentadienyl ring, n is 1, 2, 3, 4, 5 or 6, p and q are each, independently of one another, 0, 1, 2, 3, or 4

Y is an alkylene or alkylidene group having 3–7 C atoms, in which one or more H atoms may be replaced by $R^5$, and, optionally, one or more non-adjacent double bonds are present in the alkylidene group, s in each case is 1, 2, 3 or 4, r and t are each 0 or 1, while r+t is 1, $R^1$, $R^2$, $R^3$, $R^5$ and $R^6$ are each, independently of one another, H, an alkyl group having 1 to 8 C atoms, which group may be partially or completely fluorinated, a cycloalkyl or cycloalkenyl group having 3–8 C atoms or an aryl group and $R^4$ in each case is H or an alkyl group having 1–4 C atoms which may also be partially or completely fluorinated.

8. The process of claim 7, wherein other organometallic compounds, which are gaseous under gas-phase deposition conditions, are added during the deposition.

9. The method of claim 7, wherein the element of the Group VA is nitrogen, phosphorus, arsenic or antimony.

\* \* \* \* \*